US00PP08103P

United States Patent [19]

Wong

[11] Patent Number: Plant 8,103

[45] Date of Patent: Jan. 19, 1993

[54] PLUM TREE NAMED 'COMPACT FRIAR'

[76] Inventor: Henry G. Wong, 900 Jackson St., Unit 104, Oakland, Calif. 94607

[21] Appl. No.: 667,280

[22] Filed: Mar. 11, 1991

[51] Int. Cl.[5] ..... A01H 5/00

[52] U.S. Cl. ..... Plt./38.1

[58] Field of Search ..... Plt./38, 38.1

[56] References Cited

PUBLICATIONS

Lapkins, K. O., "Six Mutation Breeding" *Methods In Fruit Breeding* (Moore, J. N. et al., eds) (1983) Purdue University Press, West Lafayette, Ind. pp. 74–99.

Brooks, R. M., et al., "Plum" ('Friar' Listing) *Register of New Fruit and Nut Varieties* 1972 University of California Press, Berkeley, p. 498.

Tukey, H. B., "12 Dwarfing Rootstocks for the Plum" *Dwarfed Fruit Trees,* The Macmillan Co., N.Y. pp. 200–213.

Weinberger, J. H. "Plums" *Advances in Fruit Breeding* (Janick, J., et al., eds.) (1975) Perdue University Press, West Lafayette, Ind. pp. 336–347.

*Primary Examiner*—James R. Feyrer

[57] ABSTRACT

A plum tree named Compact Friar similar to Friar plum, of which it is a mutation, but distinguished by dwarf size of the tree.

1 Drawing Sheet

ORIGIN AND REPRODUCTION

This petition is for a new cultivar of Japanese plum (*Prunus salicina*). As research partner of a tree breeding enterprise, I directed an experimental program to breed new cultivars of stone fruits by treating budwood with cobalt 60 Picowave radiation in dosages ranging from 1,500 rads to 18,000 rads to induce mutations and then budding the treated buds onto Nemaguard peach (unpatented) rootstock in an experimental plot in San Joaquin county. One of the trees resulting from such budding, being a mutation of Friar plum (unpatented) was observed by me upon maturity to have novel characteristics. It was around half the size of regular Friar, offering a potential for high density plantings and reduced costs for cultivation and harvesting. At my direction, buds from it were then further budded on other Nemaguard rootstock in the same experimental plot. These later asexual reproductions have been true to the tree from which the buds were taken. I have personally also reproduced this new cultivar by budding onto peaches and plums in my facilities in Alameda County, Calif.

SUMMARY OF THE INVENTION

This new cultivar of plum tree is a productive regular bearer of yellowish amber fleshed, purplish black skinned, oblate fruit ripening in late July. It is similar to Friar, except that this tree is genetically dwarf in size. By its dwarf tree size and ripening of fruit in late July, it is distinguishable from Majestic M plum (U.S. Plant Pat. No. 6,975), also a mutation of Friar, which has a regular size tree and fruit ripening in late October.

PHOTOGRAPHS AND DETAILED DESCRIPTION

The accompanying photographs show two trees of this new cultivar in their fourth summer, a twig with detached leaves, and fruits both whole and divided in half, with the stone in one half.

Following is a botanical description of this new variety with fruit in firm condition based on Jul. 17, 1990 observation of two specimen trees in San Joaquin County, Calif. Color names and plate numbers are by reference to Inter-Society Color Council—National Bureau of Standards Centroid Color Charts, except where common color names are used.

Tree: Dwarf size (5 feet in 4th summer), dense, medium vigor, regular bearer, precocious, highly productive (around 50 fruits in 4th summer) form upright spreading to round with wide angle crotches on branches. Friar, in comparison, is twice as tall, less dense, more upright, with narrower angled crotches. Third generation trees of the new variety budded on myrobolan root appeared less dwarfy in the first year than those budded on Nemaguard.

Trunk: 1½ inches in diameter, normal texture of plum bark, average number of white lenticels.

Branches: ⅝ to ¾ inches in diameter, brown color, normal plum bark texture, shorter than normal internodes. A 1992 sample of internodes in Alameda County averaged 2.2 cm compared to 2.75 cm for Friar.

Leaves:

*Size.*—8 cm. long, 3 cm. wide. 1992 sample of trees in Alameda County averaged 9.5 cm long, 3.5 cm wide, very similar to Friar.

*Shape.*—Oblanceolate slightly cupped, base obtuse (some inequilateral), apex acuminate.

*Color.*—Top side moderate olive green (125), bottom side grayish yellow green (122).

*Margin.*—Serrate.

*Venation.*—Arcuate, some midribs with pinkish hue at basal end.

*Glands.*—Generally none; occasionally one on each side of petiole near leaf base, globose in form. 1992 sample of trees in Alameda County showed average of 2 glands per leaf, with a range of 0 to 3, same as Friar.

*Petiole.*—Average length 1.7 cm., mostly dark greenish yellow (103) but some pinkish.

*Stipules.*—Absent.

Flowers (as observed February 1991 in Alameda County, Calif.):

*Buds.*—Medium size, conical shape, non-pubescent.

*Flowers.*—Generally similar to Friar, midseason blooming, one to six flowers per node, each flower containing five white, medium-size petals, light yellow stamens, and yellow pistil.

*Pollination.*—Self-incompatible like Friar; a suitable pollinator is required.

Fruit: Large size averaging 4.1×4.6×4.3 cm (axial, cheek to cheek, and suture diameters); form moderately oblate; cavity 1.5×0.6 cm.; base round; apex round to truncate, some slightly depressed; suture indented by unmarked; stem averaging 0.7 cm. long, medium thickness. 1991 observations in Alameda County showed this to be similar to Friar in size, shape, uniformity and time of ripening (3rd week of July).

Skin: Thin to medium, glabrous; vivid dark purple (225) when less ripe to purplish black (235) when more ripe; no cracking; covered by bluish gray (191) bloom; peels easily but some flesh adheres to skin.

Flesh: Brilliant orange yellow (67); mild sweet flavor; mild aroma; juicy, smooth, melting; ripens evenly; eating quality very good.

Stone: Length 1.8 cm., width 1.2 cm., thickness 0.9 cm., substantially freestone, light yellowish brown color (76) when dry, obovate form, base obtuse, apex acuminate, surface rough and wrinkly, one edge grooved with the other ridged, few splits. In comparison, a 1990 sample of Friar stones were of the same size, but less uniform in shape, approximately 75% being round and only 25% oval to obovate. Fertility of stones has not been tested.

Use: Home orchards or special application in commercial orchards.

Keeping quality: Good.

Shipping quality: Unknown.

The plum tree and its fruit herein described may vary in slight detail due to difference in climate, soil, pruning, fertilization or other practices or growing conditions. The present description is of the variety as grown in an experimental plot is San Joaquin County, Calif.

I claim:

1. A new and distinct variety of plum tree, substantially as illustrated and described, identified by the characteristics enumerated above, and characterized particularly as to novelty in comparison to other plum trees by the genetically dwarf size of tree, but otherwise similar to the Friar plum tree from which it mutated.

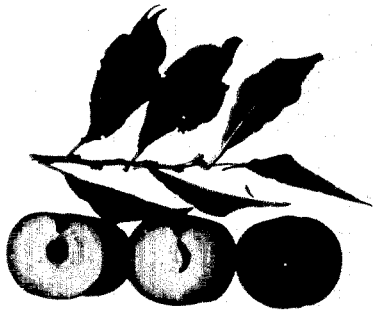
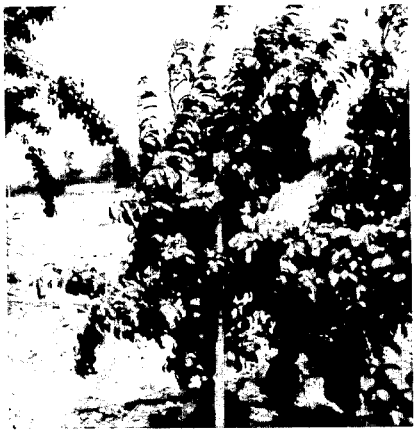

* * * * *